United States Patent [19]

Simonson

[11] Patent Number: 5,514,553
[45] Date of Patent: May 7, 1996

[54] **PRODUCTION OF MONOCLONAL ANTIBODIES TO *TREPONEMA DENTICOLA* BY HYBRIDOMA TDII, IAA11**

[75] Inventor: Lloyd G. Simonson, Deerfield, Ill.

[73] Assignee: The United States of America as Represented by the Secretary of the Navy, Washington, D.C.

[21] Appl. No.: 356,044

[22] Filed: May 22, 1989

[51] Int. Cl.⁶ .......................... G01N 33/53; G01N 33/569
[52] U.S. Cl. ...................... 435/7.22; 435/7.5; 435/7.32; 435/7.9; 435/7.92; 435/7.95; 435/172.2; 435/240.27; 436/518; 436/524; 436/528; 436/531; 530/388.2; 530/388.6
[58] Field of Search ................................ 435/7.22, 7.5, 435/7.32, 7.9, 7.92, 7.95, 172.2, 240.27; 436/518, 524, 528, 531, 800, 804; 424/1.1, 85.8, 87; 530/387, 388.2, 388.6

[56] References Cited

PUBLICATIONS

Simonson et al, "Monoclonal Antibodies that Recognize a Specific Surface Antigen of *Treponema denticola*," Infect. Immun. 56(1) pp. 60–63 (Jan. 1988).
Simonson et al, "Quantitative Relationship of *Treponema denticola* to severity of Peridontal Disease," Infect. Immun. 56(4) pp. 726–728 (Apr. 1988).

*Primary Examiner*—Toni R. Scheiner
*Attorney, Agent, or Firm*—A. David Spevack; William C. Garvert

[57] ABSTRACT

A monoclonal antibody is disclosed which is reactive to *Treponema denticola* and produced by the hybridoma deposited under ATCC HB 9966. The invention also discloses diagnostic reagents and methods for detecting *Treponema denticola* utilizing the hybridoma deposited under ATCC HB 9966.

25 Claims, 1 Drawing Sheet

PRODUCTION OF MONOCLONAL ANTIBODIES TO *TREPONEMA DENTICOLA* BY HYBRIDOMA TDII, IAA11

STATEMENT OF GOVERNMENT INTEREST

"The invention described herein may be manufactured and used by or for the Government of the United States of America for Governmental purposes without the payment of any royalties thereon or therefor."

BACKGROUND OF THE INVENTION

1. Field Of The Invention

This invention relates to monoclonal antibodies produced by hybridoma cell lines created by the fusion of myeloma cell lines with lymphocytes.

The invention further relates to methods for detecting anaerobic micro-organisms in clinical samples; more specifically the present invention relates to methods for detecting Treponema species, potential etiological agents in periodontal disease (Moore, et al. *Infection and Immunity*, 38, 1137, (1982)).

It has now been found that the fusion of a mouse myeloma cell line, X63-Ag8.653, with a BALB/c mouse lymphocyte creates a hybridoma which produces a monoclonal antibody which is capable of specifically detecting at least eight strains of *Treponema denticola*.

2. Discussion Of The Prior Art

It is possible that certain spirochetes may be etiologic agents of severe periodontitis in adults or may serve as diagnostic indicators of this disease. Moore, et al. has described the isolation of ten Treponema species from plaque samples of patients with severe periodontitis. (*Infection and Immunity*, 38, 1137 (1982)). One of the treponemes more frequently isolated from diseased sites was identified as *Treponema denticola*. *Treponema denticola* and four other oral treponemes were also found to be among the most likely causative agents of moderate periodontitis. (Moore, et al., *Infection and Immunity*, 42, 510 (1983)). The role of specific spirochetes in periodontitis is unclear, since it is difficult and time-consuming to culture, purify, and positively identify *Treponema denticola* from clinical specimens. Therefore, immunochemical assays with specific monoclonal antibodies would greatly facilitate the detection and evaluation of this spirochete in human clinical studies.

Before the use of hybridomas to produce monoclonal antibodies, species specific antibodies were made by absorbing polyclonal animal sera with cross-reacting antigens. However, antisera prepared in animals are heterogeneous, unpredictable, and very limited in supply. The advent of a classical technique to produce monoclonal antibodies (Kohler and Milstein, *Nature*, 256, 495 (1975)) has allowed for the generation of immunodiagnostic reagents which are highly specific, homogeneous, and unlimited in supply.

A simplified technique based on the Kohler and Milstein methodology for creating hybridomas that produce monoclonal antibodies was described by Fazekas de St. Groth and Scheidegger (*Journal of Immunological Methods*, 35, 1 (1980)). The conditions described by Fazekas de St. Groth and Scheidegger have been utilized frequently; these conditions were modified to obtain a hybridoma producing a monoclonal antibody specific for fourteen strains of *Bacteroides gingivalis* (Simonson, et al., *Journal of Dental Research*, 65, 95 (1986)).

In addition, these conditions were again modified to produce the monoclonal antibody of the present invention (Simonson, et al., *Infection and Immunity*, 56,, 60 (1988)).

Recently, Strosberg, et al. disclosed in U.S. Pat. No. 4,780,407 a process for the immunological determination of *Legionella pneumophilia* bacteria using a monoclonal antibody produced by a hybridoma cell-line.

SUMMARY OF THE INVENTION

It has been found that the fusion of a mouse myeloma cell line with a mouse lymphocyte creates a hybridoma cell line which produces a uniquely active monoclonal antibody. This antibody is uniquely specific for bacterial epitopes associated with the species *Treponema denticola*.

The uniquely active monoclonal antibody of the present invention may be included in diagnostic reagents and methods used to detect the oral anaerobe *Treponema denticola*.

DESCRIPTION OF THE PREFERRED EMBODIMENT

Figure 1:
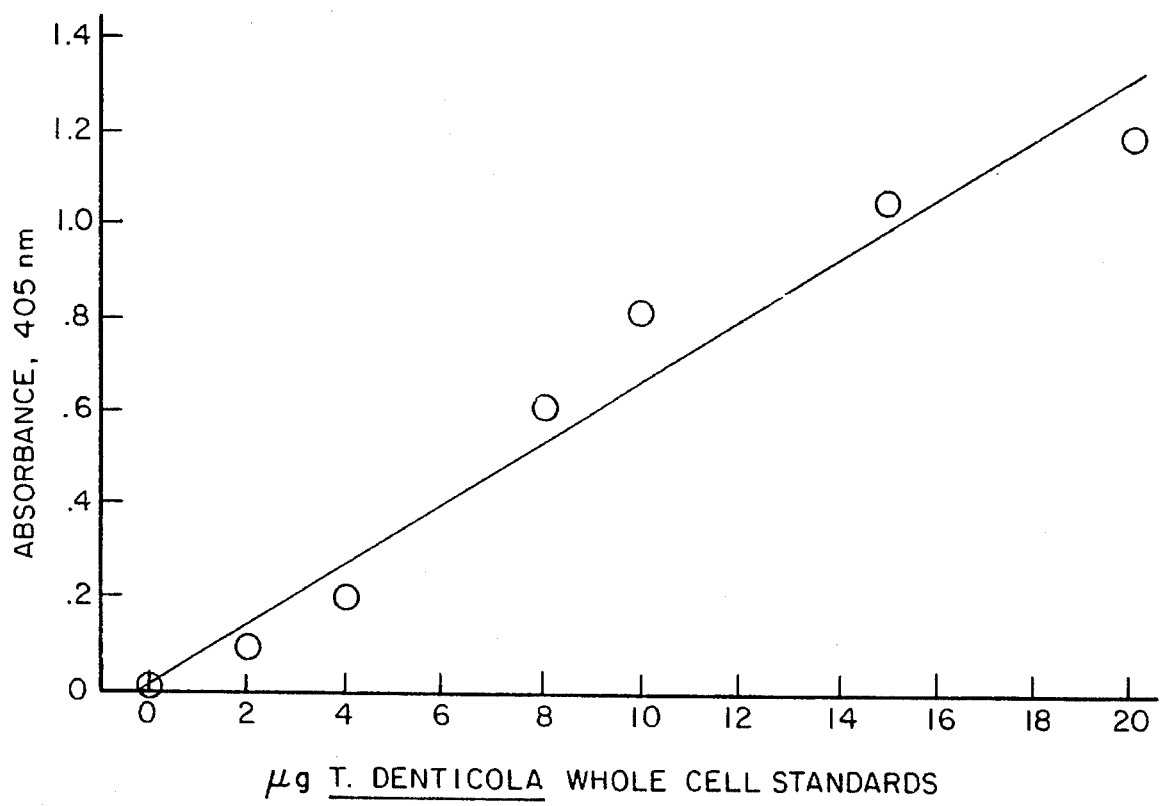
FIG. 1 illustrates biotin-avidin-enhanced ELISA absorbance measurements after a 30-min substrate incubation period in a 96-well polystyrene plate. A linear regression plot of the absorbance values is shown over a typical range of *T. denticola* standard antigen mixture used.

It has been found that, as noted above, the fusion of a mouse myeloma cell line with a mouse lymphocyte creates a hybridoma which produces a uniquely active monoclonal antibody. This hybridoma has been deposited under the provisions of the Budapest Treaty on the International Recognition of the Deposit of Microorganisms for the purposes of Patent Procedure on Jan. 12, 1989, with the American Type Culture Collection, 12301 Parklawn Dr., Rockville, Md. 20852 under accession number ATCC HB 9966. All restrictions on the availability to the public of the deposited microorganism will be irrevocably removed upon the granting of this application as a patent.

The hybridoma techniques used in this investigation were similar to those first reported by Kohler and Milstein, ibid., and as modified by de St. Groth and Scheidegger, ibid., the basic fusion protocol followed utilized Iscove's basal medium.

The unique antibody produced by the hybridoma may be directly or indirectly linked to a detectable labeling group. Indirect linkage to a detectable label may be achieved using aviding-biotin technology.

Detectable labels that may be employed in the present invention include enzymes, fluorescent labels and radionuclides. The preferred label is an enzyme that binds to the antibody at a position which does not interfere with the binding of the antibody to the antigen.

Thus, the enzyme should possess potentially reactive groups to which the antibody can be coupled without destroying enzyme activity and the enzyme should not occur naturally to an appreciable extent in the type of tissue to be assayed for the said biological substance. In addition, the enzyme should have a relatively long shelf life, a high specific activity and also be capable of being easily assayed, for example, with a visible light spectrophotometer.

Examples of enzymes which may conveniently be employed in the present invention are: maleate dehydrogenase, staphylococcal nuclease, $\delta$-5-ketosteroid isomerase, yeast alcohol dehydrogenase, yeast glucose-6-phosphate dehydrogenase, α-glycerophosphate dehydrogenase, triose phosphate isomerase, horseradish peroxidase, alkaline phosphatase, asparaginase, glucose oxidase, beta-galactosidase, ribonuclease and urease. Normally, it is preferred to purify the enzyme, for example, by dialysis against saline, before use.

A radionuclide such as $^{125}I$ or $^{32}P$ may also be used as the label.

The preparation of the enzyme-labelled antibody for use in the present invention can take place via conventional methods known in the art.

Examples of the coupling of biological substances to enzymes are described in, for example, L. A. Steinberger, Immunocytochemistry, Prentice Hall, N.J. (1974).

As pointed out above, indirect linkage of antibodies to detectable labels may be accomplished with avidin-biotin technology. The use of primary-secondary antibody techniques in tandem with avidin-biotin technology affords an assay with increased sensitivity. A review of avidin-biotin technology appears in *Analytical Biochemistry*, 171, (1988).

The invention is illustrated further by the following examples which are not to be construed as limiting the invention in scope or spirit to the specific procedures described in them.

EXAMPLE I

Production Of Monoclonal Antibody Specific For *Treponema Denticola*

1. Preparation Of Antigens

The treponemes studied (Table 1) were routinely grown in a Coy anaerobic chamber containing 80% nitrogen, 10% carbon dioxide, and 10% hydrogen, at 37° C. The cells were washed with 0.01M phosphate-0.02M $MgCl_2$ pH 7.2 buffer (PBS). Whole-cell antigens were then fixed overnight in 0.6% formalin-PBS, washed with PBS, and re-suspended in sterile 0.015 mol/L NaCl at a concentration of 10 mg (wet weight) per mL.

2. Immunization

Male and female eight-to-ten-week-old BALB/c BYJ mice were challenged with 0.05 mL whole-cell antigen preparations from *Treponema denticola* ATCC 33521 per rear foot pad, after the antigen had been mixed 1:1 (v/v) with Freund's complete adjuvant. Each animal was also initially injected intraperitoneally with 0.1 mL of the formalinized whole-cell antigen preparation (1 mg). Marginal tail vein booster injections were given 15 days later, using 0.1 mL (1 mg) of PBS washed whole-cell antigen. A final intravenous/booster of the whole-cell immunogen was always given three days prior to the hybridoma fusion.

3. Hybridoma Fusion

The X63-Ag8.653 mouse myeloma cell line was used for hybridoma fusions. Kearney, et al., *Journal of Immunology*, 123, 1548 (1979), demonstrated that this cell line had lost the ability to express its own immunoglobulins. The myeloma cells were grown to log phase and fused with donor splenocytes using pre-screened (polyethylene glycol) PEG 4000 (50% in serum-free basal medium). The cell mixture was pelleted and treated for one minute with the PEG mixture, diluted with 20 mL of culture medium containing 20% fetal bovine serum (FBS), and re-centrifuged at 200 g for five minutes. The pellet was re-suspended in Dulbecco's Modified Eagle Medium (DMEM) with 20% FBS and 2X HAT (culture medium containing hypoxanthine, aminopterin, and thymidine) and dispensed in 50 μL aliquots per well to 96-well plates. One day prior to fusion, the 96-well culture plates were seeded with $1 \times 10^5$ BALB/c splenocyte feeder cells per well in 50 μL of basal medium. Hybridomas were grown at 37° C., with humidity from 70 to 80% and carbon dioxide from 6 to 8%. Well supernatants from the initial plating were assayed by the enzyme linked immunosorbent assay (Ebersole et al., *Journal of Clinical Microbiology*, 19, 639 (1984)) (ELISA) for antibody to the appropriate *Treponema denticola* antigen preparation, as described below. Positive wells were recloned again by limiting dilution.

The hybridoma fusion resulted in somatic cell hybridomas which secreted monoclonal antibodies to surface epitopes of *Treponema denticola*. The protocol used was focused on producing monoclonal antibodies to whole-cell microbial antigens.

The hybridoma fusion resulted in macroscopic growth in 38 of the 1,152 culture wells 13 days after the fusion. Based on the strength of ELISA reactions, 18 clones were selectd for further study.

TABLE I

ELISA Specificity Of Monoclonal Antibodies

| Antigen Source | | Antibody Source | |
| --- | --- | --- | --- |
| Organism | Strain | IAAII | IACII |
| T. denticola | ATCC 33521 | 2.12 | 2.01 |
| | Ichelson | 2.22 | 2.12 |
| | D39DP1 | 1.25 | 1.25 |
| | N39 | 1.04 | 0.92 |
| | PM | 0.55 | 0.32 |
| | Ambigua | 0.11 | 0.00 |
| | TRRD | 0.09 | 0.00 |
| | IPP | 0.03 | 0.00 |
| | ATCC 33520 | 0.00 | 0.00 |
| | ATCC 35404 | 0.00 | 0.00 |
| | ATCC 35405 | 0.00 | 0.00 |
| | T32A | 0.00 | 0.00 |
| | ST10 | 0.00 | 0.00 |
| | TD2 | 0.00 | 0.00 |
| | D65BR1 | 0.00 | 0.00 |
| T. vincentii | D3A1 | 0.00 | 0.00 |
| | N9 | 0.00 | 0.00 |
| T. scoliodontum | MNII | 0.00 | 0.00 |
| T. socranskii subsp. socranskii | D34BR1 | 0.00 | 0.00 |
| | D56BR1116 | 0.00 | 0.00 |
| T. socranskii subsp. buccale | D11A1 | 0.00 | 0.00 |
| | D2B8 | 0.00 | 0.00 |
| T. socranskii subsp. paredis | D28C3 | 0.00 | 0.00 |
| | D46CPEI | 0.00 | 0.00 |
| T. pectinovorum | D36DR2 | 0.00 | 0.00 |

EXAMPLE II

Specificity Of Monoclonal Antibodies

After cloning by "limiting dilution" techniques, the monoclonal antibodies to *T. denticola* were characterized. The specificity of these antibodies was studied thoroughly by ELISA using 50 formalin-fixed whole-cell antigens (15 *T. denticola* isolates plus 35 other oral microbial isolates, as listed in Table II, below). The specific ELISA reactions with spirochete (Treponema) antigens for the monoclonal antibody from Clone IAAII are shown in Table I.

A pH 9.6 coating buffer was prepared to contain 1.59 g $Na_2CO_3$, 2.93 g $NaHCO_3$, 0.2 g, $NaN_3$ and 1000 mL distilled water. *Treponema denticola* samples were diluted as required with protein coating buffer consisting of 1.0 mL 50× panacoat protein coating solution in 50 mL coating buffer. 100 μL of the resulting antigen sample was dispersed to each well of a 96 well Immulon 2 ELISA plate. 50 μL of a coating buffer prepared by diluting 3× coating buffer 1:50 with panacoat protein coating solution was added to each well. After the antigen was added, the plate was incubated at 2°–8° C. overnight. A pH 7.4 phosphate buffer solution (PBS) was prepared to contain 8.0 g NaCl, 0.2 g $KH_2PO_4$, 2.9 g $Na_2HPO_4 \cdot 12 H_2O$, 0.2 g KCl, 0.2 g $NaN_3$ and 1000 mL distilled water. A 0.5% glutaraldehyde—PBS solution was prepared by adding 0.1 mL of 50% glutaraldehyde solution to 10 mL PBS. The plates were then spun for 15 minutes at 2000 rpm. After the plates were flicked, 100 μL of the 0.5% glutaraldehyde—PBS solution was added to each well and the plate incubated at room temperature for 15 minutes. The plates were again flicked and washed three times with a cold PBS wash solution prepared to contain 1000 mL PBS, 1.0 g bovine serum albumin (BSA), and 0.5 ml of a surfactant such as polyoxyethylene sorbitan monolaurate. 200 μL of a blocker solution prepared to contain 20 mL PBS, 0.05 g of 0.25% BSA, and 0.15 g glycine was added to each well and the plate incubated at room temperature for 30 minutes. The plate was then washed three more times with cold PBS wash solution.

To each of the wells in columns 1 and 2 was added, as a negative control, 150 μL of Iscove's Modified Dulbecco's Medium (IMDM) with supplements. 150 μL of each hybridoma supernatant was then added to all wells in columns 3 through 12. The plates were then incubated for 1 hour at 37° C. in an Enzyme-linked Immunoassay (EIA) incubator, after which they were again washed three times with cold PBS wash solution.

Biotin labelled second antibody conjugate was prepared by diluting one part biotin labelled-affinity purified Rabbit anti-mouse IgG in 5000 parts 0.1% BSA—1% normal rabbit serum/PBS solution. 100 μL of this resulting solution was then added to each well of the ELISA plate and the plate incubated for one hour at 37° C.

The plate was subsequently washed three times with cold PBS wash solution. An alkaline phosphatase-avidin conjugate solution was prepared to contain 0.1 mL alkaline phosphatase-avidin conjugate in 500 mL 0.1% BSA—1% normal rabbit serum/PBS solution. 100 μL of this conjugate solution was then added to each of the wells. The plate was again incubated for one hour at 37° C., washed three times with cold PBS wash solution and then three times with distilled water.

Diethanolamine buffer was prepared by mixing 98 g diethanolamine, 800 mL water, 0.2 g sodium azide, and 0.1 g $MgCl_2 \cdot 6H_2O$, adding sufficient 1 M HCl to attain a pH of 9.8 and then adding additional water to a volume of 1 liter. This solution is then stored at 4° C. in the dark and allowed to warm to room temperature prior to use.

An alkaline phosphatase substrate solution was prepared immediately prior to use by dissolving one 5 mg tablet of disodium p-nitrophenyl phosphate into 5 mL of the warmed 10% diethanolamine buffer.

200 μL of the alkaline phosphatase substrate solution was added to each well of the plate which was subsequently incubated in the dark at room temperature until a yellow color developed. After each plate has developed, 50 μL of a 2N NaOH stopping solution was added to each well.

Optical density measurements were then determined in a Titertek Multiskan MC spectrophotometer at a wave length of 405 nm. The results are shown in Table II.

Monoclonal antibodies IAAII and IACII reacted with 8 of 15 and 5 of 15 *T. denticola* strains, respectively (Tables I and II). Cross-reactions with 25 strains of non-treponemal oral bacteria were not observed (Table II).

Hybridoma TDII, IAA11 has been deposited with the American Type Culture Collection under accession number ATCC HB 9966.

TABLE II

ELISA Specificities Of Various Oral Bacteria

| Antigen (No. Tested) | No. positive For MAB | |
|---|---|---|
| | IAA11 | IAC11 |
| *Treponema denticola* (15) | 8 | 5 |
| *T. vincentii* (2) | 0 | 0 |
| *T. scoliodontum* (1) | 0 | 0 |
| *T. socranskii* (6) | 0 | 0 |
| *T. rectinovorum* (1) | 0 | 0 |
| *Bacteroides gingivalis* (9) | 0 | 0 |
| *B. intermedius* (4) | 0 | 0 |
| *B. asaccharolyticus* (1) | 0 | 0 |
| *B. melaninogenicus* (1) | 0 | 0 |
| *B. macacae* (1) | 0 | 0 |
| *Fusobacterium nucleatum* (1) | 0 | 0 |
| *Streptococcus mutans* (2) | 0 | 0 |
| *Capnocytophaga ochracea* (2) | 0 | 0 |
| *Haemophilus actinomycetemcomitans* (4) | 0 | 0 |

EXAMPLE III

Clinical Determination Of *T. denticola* Antigen In Plaque

1. Sample Collection And Preparation

Clinical samples from two separate human populations were studied. A military population sample consisted of 65 volunteers at a Navy dental clinic. The military population parameters are presented in Table III. A university population sample included 36 volunteers at the periodontics clinic of Northwestern University Dental School. The parameters of the university volunteers are shown in Table IV. Each population was divided into three groups according to periodontal disease severity and pocket depth at the sample site. Periodontally healthy subjects exhibited gingival sulcus depths of less than 4 mm, little or no gingival inflammation, and no radiographic evidence of alveolar bone loss. The remaining two groups within both populations were subjects with American Dental Association case type III and IV periodontitis. The moderate periodontitis patients exhibited moderate gingival inflammation, bleeding upon probing 4- to 6-mm pockets, and radiographic evidence of early to moderate alveolar bone loss. The advanced periodontitis patients exhibited moderate to severe gingival inflammation, bleeding upon probing, multiple sites probing greater than 6 mm, and radiographic evidence of generalized, moderate to severe alveolar bone loss. None of the subjects had a history of significant medical problems as determined by a health questionnaire, and none had received dental treatment including scaling and root planning or antibiotic therapy for at least 6 months before sampling.

The pocket depth at the sample site was measured to the nearest millimeter with a Michigan O probe. Total plaque (both subgingival and supragingival) was studied in the military population, whereas only subgingival plaque samples were obtained from the university population. Plaque specimens from healthy subjects were pooled from interproximal sites to have sufficient amounts for assay measurements. Plaque samples from the disease sites were from single sites. All plaque samples were collected with sterile curettes and placed immediately into vials containing formalinized coating buffer.

Each plaque sample was dispersed by sonicating for 5 s at 32 to 39 W (25 to 30% of the 130-W average output) with a Heat Systems-Ultrasonics model WI40 sonifier. The wet weight was determined spectrophotometrically by measuring absorbance of the plaque suspension at 420 nm. The absorbance values were then compared with a standard curve constructed from serial dilutions of preweighed pooled plaque samples.

2. Quantitative Determination Of Antigen Utilizing Biotin-Avidin Primary-Secondary Antibody Enhanced ELISA A pH 9.6 coating buffer was prepared as in Example II above. *Treponema denticola* samples were diluted as required with protein coating buffer as prepared above. 100 µL of the resulting antigen sample was dispersed to each well of a 96 well Immulon 2 ELISA plate. 50 µL of a coating buffer prepared by diluting 3× coating buffer 1:50 with panacoat protein coating solution was added to each well. After the antigen was added, the plate was incubated at 2°–8° C. overnight. A pH 7.4 phosphate buffer solution (PBS) and a 0.5% glutaraldehyde—PBS were prepared as described above. The plates were then spun for 15 minutes at 2000 rpm. After the plates were flicked, 100 µL of the 0.5% glutaraldehyde—PBS solution was added to each well and the plate incubated at room temperature for 15 minutes. The plates were again flicked and washed three times with a cold PBS wash solution. 200 µL of a blocker solution was added to each well and the plate incubated at room temperature for 30 minutes. The plate was then washed three more times with cold PBS wash solution.

To each of the wells in columns 1 and 2 was added, as a negative control, 150 µL of Iscove's Modified Dulbecco's Medium (IMDM) with supplements. 150 µL of hybridoma supernatant containing murine monoclonal antibody IAAII was then added to all wells in columns 3 through 12. The plates were then incubated for 1 hour at 37° C. in an Enzyme-linked Immunoassay (EIA) incubator, after which they were again washed three times with cold PBS wash solution. 100 µL of the biotin labeled second antibody conjugate solution was then added to each well of the ELISA plate and the plate incubated for one hour at 37° C.

The plate was subsequently washed three times with cold PBS wash solution. 100 µL of the alkaline phosphatase-avidin conjugate solution was then added to each of the wells. The plate was again incubated for one hour at 37° C., washed three times with cold PBS wash solution and then three times with distilled water.

200 µL of the freshly prepared alkaline phosphatase substrate solution was added to each well of the plate which was subsequently incubated in the dark at room temperature until a yellow color developed. After each plate has developed, 50 µL of a 2N NaOH stopping solution was added to each well.

Optical density measurements were then determined in a Multiskan MC spectrophotometer at a wave length of 405 nm.

The mean *T. denticola* antigen equivalents per milligram of plaque was determined for each of the three pocket depth groups in the two human populations studied. A one-way analysis of variance F test was used to test the hypothesis that the mean *T. denticola* content per milligram of plaque was different for each of the pocket depth groups in each population. Each analysis of variance generated an F value which was converted to a significance level by using a table of programmed F values. Significant outcomes ($P<0.05$) were further compared by a Fisher least-significant-difference, post hoc multiple-range test. Only within-population comparisons were made, since each of the populations was studied separately with no attempt to normalize subjects between the two distinct population samples.

The sensitivity of the biotin-avidin-enhanced ELISA is shown in FIG. 1. Each assay plate included a similar standard curve over the 0- to 20-µg range of *T. denticola* whole cell antigen standards. The assay was essentially linear over this range, and the lower limit of sensitivity was in the 2- to 4-µg range. Negative control wells, incubated with the hybridoma growth medium, showed very little background color, and this background was used to blank the automated plate reader to compensate for extraneous color development in the absorbance measurements.

The microgram quantities of *T. denticola* antigen equivalents (estimated from the antigen standard mixture) per milligram of plaque from the military population are shown in Table III.

The quantitative estimations of *T. denticola* antigen content in subgingival plaque samples from volunteers at a university clinic are shown in Table II.

All sites were also found to be positive for some quantity of *T. denticola* antigen. Several members of the intermediate-pocket-depth group were found to have *T. denticola* antigen quantities greater than the mean value for the deep-pocket group. The mean gingival index values for the intermediate and deep-pocket groups were quite similar to those for the healthy control group. Other population parameters are summarized in Tables III and IV. The ratios of micrograms of *T. denticola* per milligram of plaque in the deep-pocket groups to those of the healthy and intermediate groups were about 2:1 in both populations.

TABLE III

Quantitative Estimation Of *T. denticola* Antigen In Plaque From Male Military Volunteers

| Test Group | No. of Patients | Pocket Depth (mm) (+SD) | Age (yr) (+SD) | Age Range (yr) | *T. denticola* content (µg/mg of plaque) Mean (+SD) | Range |
|---|---|---|---|---|---|---|
| Normal <4 mm | 26 | 2.8 (0.6) | 20.8 (3.6) | 17–33 | 2.7 (2.9) | 0.5–15.5 |
| Intermediate 4–6 mm | 24 | 4.9 (0.8) | 28.7 (2.8) | 25–34 | 4.4 (5.2) | 1.1–26.6 |
| Deep >6 mm | 15 | 7.7 (0.9) | 25.9 (3.8) | 19–33 | 13.4 (9.3) | 1.5–33.4 |

TABLE IV

Quantitative Estimation Of *T. denticola* Antigen Content In Subgingival Plaque From University Volunteers

| Test Group | No. of Patients (men/women) | Pocket Depth (mm) (+SD) | Age (yr) (+SD) | Age Range (yr) (+SD) | *T. denticola* content (µg/mg of plaque) Mean (+SD) | Range |
|---|---|---|---|---|---|---|
| Normal, <4 mm | 10 (8/2) | 2.6 (0.5) | 41.5 (10.3) | 27–63 | 74.3 (48.7) | 8.6–165.9 |
| Intermediate, 4–6 mm | 15 (8/7) | 5.1 (0.7) | 50.1 (14.1) | 32–71 | 68.2 (61.1) | 5.5–283.6 |
| Deep, >6 mm | 11 (7/4) | 7.5 (1.0) | 47.8 (16.3) | 33–72 | 139.5 (122.8) | 5.2–361.9 |

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A monoclonal antibody reactive to *Treponema denticola* produced by the hybridoma deposited under ATCC HB 9966.

2. A diagnostic reagent comprising the monoclonal antibody of claim 1 linked directly or indirectly to a detectable label.

3. A diagnostic reagent according to claim 2, wherein the detectable label is an enzyme.

4. A diagnostic reagent according to claim 2, wherein the detectable label is a fluorescent marker.

5. A diagnostic reagent according to claim 2, wherein the detectable label is a radionuclide.

6. A diagnostic reagent according to claim 2, wherein the monoclonal antibody of claim 1 is indirectly linked to a detectable label via a secondary antibody reactive to the monoclonal antibody of claim 1 and bound directly or indirectly to a detectable label.

7. A diagnostic reagent according to claim 6, wherein the detectable label is an enzyme.

8. A diagnostic reagent according to claim 6, wherein the detectable label is a fluorescent marker.

9. A diagnostic reagent according to claim 6, wherein the detectable label is a radionuclide.

10. A diagnostic reagent according to claim 6, wherein the secondary antibody is covalently linked to a hapten and the detectable label is covalently linked to an antihapten.

11. A diagnostic reagent according to claim 10, wherein the detectable label is an enzyme.

12. A diagnostic reagent according to claim 10, wherein the detectable label is a fluorescent marker.

13. A diagnostic reagent according to claim 10, wherein the detectable label is a radionuclide.

14. A diagnostic reagent according to claim 11 wherein the hapten is biotin and the antihapten is avidin or streptavidin.

15. A diagnostic reagent according to claim 14, wherein the detectable label is an enzyme.

16. A diagnostic reagent according to claim 14, wherein the detectable label is a fluorescent marker.

17. A diagnostic reagent according to claim 14, wherein the detectable label is a radionuclide.

18. A method for detecting *Treponema denticola* comprising the steps of:

(a) contacting a media suspected to contain *Treponema denticola* with the monoclonal antibody of claim 1 linked directly or indirectly to a detectable label; and (b) detecting the label, whereby the presence of *Treponema denticola* in the media is determined.

19. A method according to claim 18, wherein the detectable label is an enzyme.

20. A method according to claim 18, wherein the detectable label is a fluorescent marker.

21. A method according to claim 18, wherein the detectable label is a radionuclide.

22. A method for detecting *Treponema denticola* comprising the steps of:

(a) contacting a media suspected to contain *Treponema denticola* with the monoclonal antibody of claim 1;

(b) contacting an antibody reactive to the monoclonal antibody of claim 1 and directly or indirectly linked to a detectable label with the media suspected to contain *Treponema denticola;* and (c) detecting the label, whereby the presence of *Treponema denticola* in the media is determined.

23. A method according to claim 22, wherein the detectable label is an enzyme.

24. A method according to claim 22, wherein the detectable label is a fluorescent marker.

25. A method according to claim 22, wherein the detectable label is a radionuclide.

* * * * *